United States Patent [19]

Nickel et al.

[11] Patent Number: 5,091,427
[45] Date of Patent: Feb. 25, 1992

[54] PIPERAZINEDIONES HAVING A PSYCHOTROPIC ACTION

[75] Inventors: Wolf-Ulrich Nickel, Bad Soden am Taunus; Rainer Henning, Hattersheim am Main; Wolfgang Rüger, Kelkheim; Ulrich Lerch, Hofheim am Taunus; Hansjörg Urbach, Kronberg/Taunus; Franz Hock, Dieburg; Gabriele Wiemer, Kronberg/Taunus, all of Fed. Rep. of Germany

[73] Assignee: Hoechst Aktiengesellschaft, Frankfurt am Main, Fed. Rep. of Germany

[21] Appl. No.: 401,842

[22] Filed: Sep. 1, 1989

[30] Foreign Application Priority Data

Sep. 3, 1988 [DE] Fed. Rep. of Germany ....... 3830096

[51] Int. Cl.$^5$ .................. A61K 31/495; C07D 241/36
[52] U.S. Cl. .................................... 514/249; 514/250; 544/230; 544/344
[58] Field of Search ............... 544/263, 230, 349, 344, 544/346, 347; 514/252, 250, 249

[56] References Cited

FOREIGN PATENT DOCUMENTS 7003463 9/1970 Netherlands ................... 544/346

OTHER PUBLICATIONS

Donalds Medical Dictionary, p. 296, 1958.
Cecil's Textbook in Medicine, p. 1979, 1983.
Khandelwal et al., "Agents Acting on CNS . . . ", Ind. J. Chem. 16B, 1015-18 (1978).
Occelli et al., "CNS Active Substance . . . ", CA 101:211099j (1984).
Kasafirek et al., "Spiro-2,5-Piperazinedione . . . ", CA 106: 33473s (1987).
Tanhiguchi (Formula IV) CA 105: 191590m (1986).
Berlhet (Formula IV) CA 105: 191593q (1986).
Arnold B. Scheibel et al., The Biological Substrates of Alzheimer's Disease, Academic Press, 1986, London, New York 3ff.
U. Schindler et al., Nootropic Drugs: Animal Models for Studying Effects on Cognition, Drug Development Research 4:567-576 (1984).
R. T. Bartus, et al., Logical Principles for the Development of Animal Models of Age-Related Memory Impairments, Assessment in Geriafric Psychopharmacology, published by Mark Pauley Associates, Inc., 88 Main Street, New Cannan, Conn., U.S.A., Dec. 1983, pp. 263-299.
G. Pepeu, The Relationship Between the Behavioral Effects of Cognition-Enhancing Drug and Brain Acetylcholine, Pharmacopsychiat, 22, 116-119, (1989).

Primary Examiner—C. Warren Ivy
Assistant Examiner—Celia Chang
Attorney, Agent, or Firm—Finnegan, Henderson, Farabow, Garrett, and Dunner

[57] ABSTRACT

The invention relates to compounds of the formula I

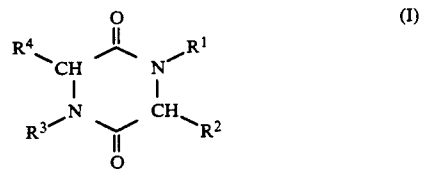

in which $R^1$, $R^2$ and $R^4$ represent optionally substituted aliphatic, alicyclic, alicyclic-aliphatic, aromatic, araliphatic, heteroaromatic or heteroaromatic-aliphatic radicals, with $R^2$, if not already covered by the above-mentioned definitions, denoting the side-chain, which is protected if necessary, of a naturally occurring α-amino acid, $R^4$ can additionally represent

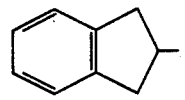

$R^3$ denotes an optionally substituted aliphatic, alicyclic, aromatic or araliphatic radical, or $R^3$ and $R^4$ form, together with the atoms carrying them, a mono-, bi- or tricyclic heterocyclic ring system, agents containing these, and the use thereof as pharmaceuticals having a psychotropic action for the prophylaxis of disorders of the central nervous system, especially having a nootropic action for the treatment of cognitive dysfunctions.

11 Claims, No Drawings

PIPERAZINEDIONES HAVING A PSYCHOTROPIC ACTION

The invention relates to new 1,4-piperazine-2,5-diones, to agents containing these, and to the use thereof as pharmaceuticals having a psychotropic action for the treatment and prophylaxis of disorders of the central nervous system, especially having a nootropic action for the treatment of cognitive dysfunctions.

It has been disclosed that (3S)-3-(2-methylpropyl)-1,4-piperazine-2,5-dione (cyclo(Leu-Gly)) has an influence on the central nervous system, especially in diminishing the tolerance to morphine (J. Pharmacol. Exp. Ther. 218 (1981) 404, WP 800-216) and as an antagonist in puromycin-induced amnesia (Pharmacol., Biochem. Behav. 10 (1979) 787; Pharmacol., Biochem. Behav. 8 (1978) 93; Jap. Pat. J5 4073-133).

Furthermore, piperazine-2,5-diones are described, for example, as analgesics (J5 8083-682-A, J5 9073-574-A), as antiulcer agents (EP 008,186, US 3,976,773) and as PAF antagonists (EP 181,152).

The invention has the object of finding new compounds having an antiamnesic action.

This object is achieved according to the invention by the compounds of the formula I

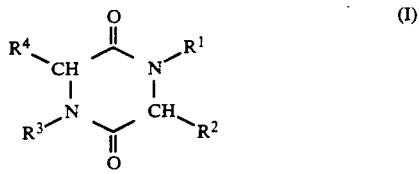

in which $R^1$ denotes hydrogen, an optionally substituted aliphatic radical having 1-21 carbon atoms, an optionally substituted alicyclic radical having 3-20 carbon atoms, an optionally substituted alicyclic-aliphatic radical having 4-20 carbon atoms, an optionally substituted aromatic radical having 6-12 carbon atoms, an optionally substituted araliphatic radical having 7-32 carbon atoms, an optionally substituted heteroaromatic or heteroaromatic-($C_1$-$C_8$)-aliphatic radical having 5-12 ring atoms, $R^2$ denotes hydrogen, an optionally substituted aliphatic radical having 1-21 carbon atoms, an optionally substituted alicyclic radical having 3-20 carbon atoms, an optionally substituted alicyclic-aliphatic radical having 4-20 carbon atoms, an optionally substituted aromatic radical having 6-12 carbon atoms, an optionally substituted araliphatic radical having 7-32 carbon atoms, an optionally substituted heteroaromatic or heteroaromatic-($C_1$-$C_8$)-aliphatic radical having 5-12 ring atoms, or, if not already covered by the abovementioned definitions, the side-chain, which is protected if necessary, of a naturally occurring α-amino acid, $R^3$ denotes hydrogen, an optionally substituted aliphatic radical having 1-21 carbon atoms, an optionally substituted alicyclic radical having 3-20 carbon atoms, an optionally substituted aromatic radical having 6-12 carbon atoms, an optionally substituted araliphatic radical having 7-32 carbon atoms, $R^4$ denotes hydrogen, an optionally substituted aliphatic radical having 1-21 carbon atoms, an optionally substituted alicyclic radical having 3-20 carbon atoms, an optionally substituted alicyclic-aliphatic radical having 4-20 carbon atoms, an optionally substituted aromatic radical having 6-12 carbon atoms, an optionally substituted araliphatic radical having 7-32 carbon atoms, an optionally substituted heteroaromatic or heteroaromatic-($C_1$-$C_8$)-aliphatic radical having 5-12 ring atoms, represents

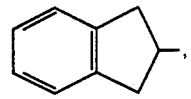

or $R^3$ and $R^4$ form, together with the atoms carrying them, a mono-, bi- or tricyclic heterocyclic ring system having 3 to 15 ring carbon atoms.

An optionally substituted aliphatic radical is to be understood as an aliphatic acyclic radical, i.e. a radical having an open, straight or branched carbon chain, such as, for example, alkyl, alkenyl, alkynyl and corresponding polyunsaturated radicals. It is preferably unsubstituted or monosubstituted, for example by hydroxyl, alkoxy, halogen, amino, alkanoylamino, alkoxycarbonylamino, arylalkoxycarbonylamino, arylalkylamino, alkylamino, dialkylamino, alkylthio, arylthio, carboxyl, carbamoyl, alkoxycarbonyl, alkanoyloxy, alkoxycarbonyloxy, aroyloxy or aryloxycarbonyloxy.

An optionally substituted alicyclic radical, and the corresponding optionally substituted alicyclic-aliphatic radical which is linked via an open carbon chain, is a preferably mono- to pentacyclic isocyclic non-aromatic radical which has single bonds or unsymmetrically distributed double bonds, and can also be branched (i.e. carry open-chain aliphatic side-chains) and which is linked via a ring carbon atom or a side-chain carbon atom. It is preferably unsubstituted. Where a radical of this type contains more than one ring, they are fused, spiro-linked or isolated. Examples of radicals of this type are cycloalkyl, cycloalkenyl, cycloalkylalkyl, bicycloalkyl, tricycloalkyl and radicals derived from mono-, bi- or oligocyclic terpenes, such as menthyl, isomenthyl, bornyl, caranyl, epibornyl, epiisobornyl, isobornyl, neomenthyl, neoisomenthyl, pinanyl, thujanyl; they are preferably unsubstituted (aliphatic side-chains are not substituents according to the present definition).

An optionally substituted aromatic radical is preferably aryl such as phenyl, biphenylyl or naphthyl, which is optionally mono-, di- or trisubstituted as indicated on page 8 for aryl. Radicals derived from aryl, such as aralkyl, aryloxy, arylthio or aroyl, preferably benzoyl, can be substituted like aryl.

An optionally substituted heteroaromatic radical is preferably an aromatic mono- or bicyclic heterocyclic radical having 5 to 7 or 8 to 12, respectively, preferably up to 10, ring atoms, of which 1 to 2 ring atoms represent sulfur or oxygen atoms and/or of which 1 to 4 ring atoms represent nitrogen atoms, such as, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiaolyl or isothiazolyl. These radicals can also be partially or completely hydrogenated. A heteroaromatic radical, and the corresponding heteroaromatic-aliphatic radical, can be substituted as defined below.

An optionally substituted araliphatic radical is to be understood as, in particular, aralkyl radicals such as arylalkyl, diarylalkyl, indanyl or fluorenyl, in which aryl is as defined below and can be substituted in the manner indicated there.

$R^3$ and $R^4$ can form, together with the atoms carrying them, a mono-, bi- or tricyclic heterocyclic ring system which has 3 to 15 ring carbon atoms and has in the ring, preferably, up to 2 sulfur atoms and up to 2 nitrogen atoms, in particular up to 1 sulfur atom.

Particularly suitable ring systems of this type are those from the following group:

pyrrolidine (O); thiazolidine (R); tetrahydroisoquinoline (A); decahydroisoquinoline (B); octahydroindole (C); indoline (Q); octahydrocyclopenta[b]pyrrole (D); 2-azaspiro[4.5]decane (E); 2-azaspiro[4.4]nonane (F); spiro-[(bicyclo[2.2.1]heptane)-2,3'-pyrrolidine](G); spiro [(bicyclo[2.2.2]octane)-2,3'-pyrrolidine](H); 2-azatricyclo[4.3.0.1$^{6,9}$]decane (I); decahydrocyclohepta[b]pyrrole (J); octahydroisoindole (K); octahydrocyclopenta-[c]pyrrole (L)-; 2,3,3a,4,5,7a-hexahydroindole (M); 2-azabicyclo[3.1.0]hexane (N); 1,2,3,3a,4,6a-hexahydrocyclopenta[b]pyrrole (P), all of which can optionally be substituted. Pyrrolidine (O) and thiazolidine (R) can be monosubstituted, for example, by ($C_6$–$C_{12}$)-aryl (phenyl, 2-hydroxyphenyl etc.), ($C_6$–$C_{12}$)-arylmercapto (such as phenylmercapto) or ($C_3$–$C_7$)-cycloalkyl (such as cyclohexyl). A corresponding statement applies to the other ring systems. However, the unsubstituted systems are preferred.

In the case of compounds of the formula I which have more than one chiral atom, suitable are all the possible diastereomers as racemates or enantiomers, or mixtures of various diastereomers.

The suitable heterocyclic ring systems have the following structural formulae:

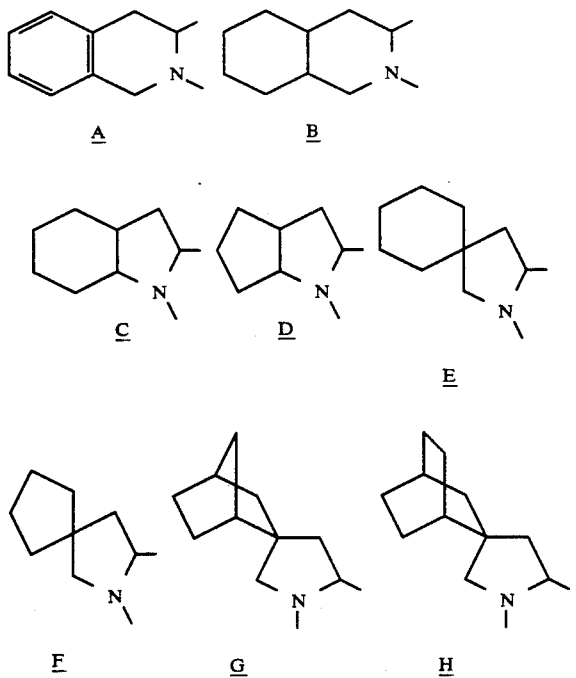

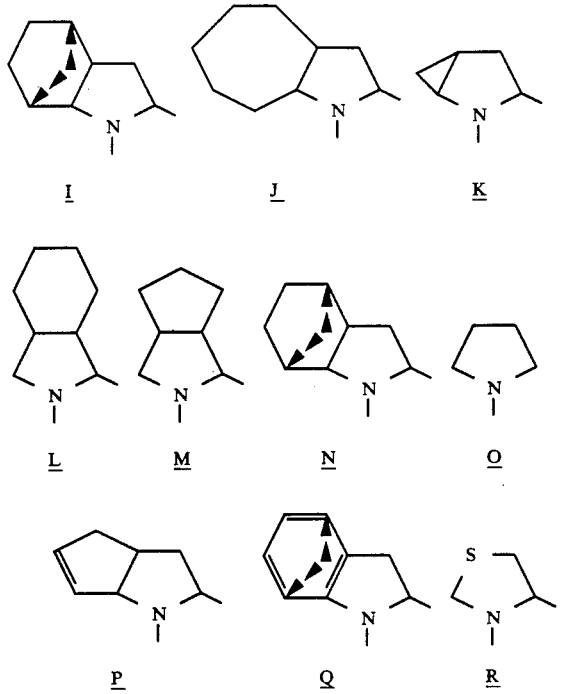

A preferred embodiment comprises compounds of the formula I in which $R^1$ denotes hydrogen; ($C_1$–$C_{18}$)-alkyl; an aliphatic acyclic radical of the formula $C_aH_{(2a-b+1)}$, in which double bonds, if the number thereof exceeds 1 are not cumulative, a represents an integer 2 to 18, and b represents an even number 2 to a; a mono-, di- or tricyclic nonaromatic, optionally branched hydrocarbon radical of the formula $C_cH_{(2c-d-1)}$, in which c represents an integer 3 to 20, and d represents an even number 0 to (c-2); ($C_6$–$C_{12}$)-aryl which can be mono-, di- or trisubstituted by ($C_1$–$C_8$)-alkyl, ($C_1$–$C_4$)-alkoxy, hydroxyl, halogen, nitro, amino, aminomethyl, ($C_1$–$C_4$)-alkylamino, di-($C_1$–$C_4$)-alkylamino, ($C_1$–$C_4$)-alkanoylamino, methylenedioxy, carboxyl, cyano and/ or sulfamoyl; amino-($C_1$–$C_8$)-alkyl; ($C_1$–$C_4$)-alkanoylamino-($C_1$–$C_8$)-alkyl; ($C_7$–$C_{13}$)-aroylamino-($C_1$–$C_8$)-alkyl; ($C_1$–$C_4$)-alkoxycarbonylamino-($C_1$–$C_8$)-alkyl; ($C_6$–$C_{12}$)-aryl-($C_1$–$C_4$)-alkoxycarbonylamino-($C_1$–$C_8$)-alkyl; ($C_6$–$C_{12}$)-aryl-($C_1$–$C_4$)-alkylamino-($C_1$–$C_8$)-alkyl; ($C_1$–$C_4$)-alkylamino-($C_1$–$C_8$)-alkyl; di-($C_1$–$C_4$)-alkylamino-($C_1$–$C_8$)-alkyl; guanidino-($C_1$–$C_8$)-alkyl; ($C_1$–$C_4$)-alkylthio-($C_1$–$C_8$)-alkyl; ($C_6$–$C_{12}$)-arylthio-($C_1$–$C_8$)-alkyl or ($C_6$–$C_{12}$)-aryloxy-($C_1$–$C_8$)-alkyl, both of which can be substituted in the aryl moiety as described above; carboxy-($C_1$–$C_{17}$)-alkyl, ($C_1$–$C_4$)-alkoxycarbonyl-($C_1$–$C_{17}$)-alkyl, carbamoyl-($C_1$–$C_{17}$)-alkyl, ($C_1$–$C_4$)-mono- or -di-alkylcarbamoyl-($C_1$–$C_{17}$)-alkyl, where alkyl is optionally substituted by ($C_6$–$C_{12}$)-aryl;

$R^2$ denotes hydrogen; ($C_1$–$C_{18}$)-alkyl; an aliphatic acyclic radical of the formula $C_aH_{(2a-b+1)}$, in which double bonds, if the number thereof exceeds 1, are not cumulative, a represents an integer 2 to 18, and b represents an even number 2 to a; a mono-, di-, tri-, tetra- or pentacyclic non-aromatic, optionally branched hydrocarbon radical of the formula $C_cH_{(2c-d-1)}$, in which c represents an integer 3 to 20, and d represents an even number 0 to (c-2); $(C_6-C_{12})$-aryl; $(C_6-C_{12})$-aryl-$(C_1-C_8)$-alkyl or $(C_7-C_{13})$-aroyl-$(C_1-C_8)$-alkyl, each of which can be substituted in the aryl moiety as described above; mono- or bicyclic, optionally partially hydrogenated heteroaryl or heteroaryl-$(C_1-C_8)$-alkyl having 5-7 or 8-10 ring atoms, of which up to 9 ring atoms represent carbon and 1 to 2 ring atoms represent sulfur or oxygen and/or 1 to 4 ring atoms represent nitrogen, each of which can be substituted in the heteroaryl moiety as described above for aryl; or, if not yet covered, the optionally protected side-chain of a naturally occurring α-amino acid of the formula $R^1$—CH(NH$_2$)—COOH; and $R^3$ and $R^4$ form, together with the atoms carrying them, a mono-, bi- or tricyclic heterocyclic ring system having 3 to 15 ring carbon atoms.

Particularly preferred compounds of the formula I are those in which $R^1$ denotes hydrogen; $(C_1-C_8)$-alkyl; $(C_2-C_6)$-alkenyl; $(C_3-C_9)$-cycloalkyl; $(C_6-C_{12})$-aryl which can be mono-, di- or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl, mono- or bicyclic heteroaryloxy having 5-7 or 8-10 ring atoms, respectively, of which 1 to 2 ring atoms represent sulfur or oxygen atoms and/or 1 to 4 ring atoms represent nitrogen, which can be substituted as described above for aryl; amino-$(C_1-C_4)$-alkyl; $(C_1-C_4)$-alkanoylamino-$(C_1-C_4)$-alkyl; $(C_7-C_{13})$-aroylamino-$(C_1-C_4)$-alkyl; $(C_1-C_4)$-alkoxycarbonylamino-$(C_1-C_4)$-alkyl; $(C_6-C_{12})$-aryl-$(C_1-C_4)$-alkoxycarbonylamino-$(C_1-C_4)$-alkyl; $(C_6-C_{12})$-aryl-$(C_1-C_4)$-alkylamino-$(C_1-C_4)$-alkyl; $(C_1-C_4)$-alkylamino-$(C_1-C_4)$-alkyl; di-$(C_1-C_4)$-alkylamino-$(C_1-C_4)$-alkyl; guanidino-$(C_1-C_4)$-alkyl; $(C_1-C_4)$-alkylthio-$(C_1-C_4)$-alkyl; $(C_6-C_{12})$-arylthio-$(C_1-C_4)$-alkyl which can be substituted in the aryl moiety as described above for aryl; carboxy-$(C_1-C_4)$-alkyl; carbamoyl-$(C_1-C_4)$-alkyl; $(C_1-C_4)$-alkoxy-carbonyl-$(C_1-C_4)$-alkyl; $(C_6-C_{12})$-aryloxy-$(C_1-C_4)$-alkyl, which can be substituted in the aryl moiety as described above for aryl, $R^2$ denotes hydrogen; $(C_1-C_6)$-alkyl; $(C_2-C_6)$-alkenyl; $(C_2-C_6)$-alkynyl; $(C_3-C_9)$-cycloalkyl; $(C_5-C_9)$-cycloalkenyl; $(C_3-C_9)$-cycloalkyl-$(C_1-C_4)$-alkyl; $(C_5-C_9)$-cycloalkenyl-$(C_1-C_4)$-alkyl; optionally partially hydrogenated $(C_6-C_{12})$-aryl which can be substituted as described above for $R^1$; $(C_6-C_{12})$-aryl-$(C_1-C_4)$-alkyl or $(C_7-C_{13})$-aroyl-$(C_1$ or $C_2)$-alkyl, both of which can be substituted like the preceding aryl; mono- or bicyclic, optionally partially hydrogenated heteroaryl having 5-7 or 8-10 ring atoms, respectively, of which 1 to 2 ring atoms represent sulfur or oxygen atoms and/or 1 to 4 ring atoms represent nitrogen atoms, which can be substituted like the preceding aryl, or the optionally protected side-chain of a naturally occurring α-amino acid $R^1$—CH(NH$_2$)—COOH; and $R^3$ and $R^4$ have the abovementioned meaning.

Compounds of the formula I which may be especially mentioned are those in which $R^1$ denotes hydrogen; $(C_1-C_8)$-alkyl; $(C_2-C_6)$-alkenyl; $(C_3-C_9)$-cycloalkyl; amino-$(C_1-C_4)$-alkyl; $(C_2-C_5)$-acylamino-$(C_1-C_4)$-alkyl; $(C_7-C_{13})$-aroylamino-$(C_1-C_4)$-alkyl; $(C_1-C_4)$-alkoxycarbonylamino-$(C_1-C_4)$-alkyl; $(C_1-C_4)$-alkoxycarbonyl-$(C_1-C_{10})$-alkyl, carbamoyl-$(C_1-C_{10})$-alkyl, $(C_1-C_4)$-mono- or -di-alkylcarbamoyl-$(C_1-C_{10})$-alkyl, where alkyl is optionally substituted by phenyl; $(C_6-C_{12})$-aryl-$(C_1-C_6)$-alkyl; $(C_6-C_{12})$-aryl-$(C_1-C_4)$-alkoxycarbonylamino-$(C_1-C_4)$-alkyl; $(C_6-C_{12})$-aryl, which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy; especially hydrogen, methyl, ethyl, tert.-butoxycarbonylamino-$(C_1-C_4)$-alkyl, benzoyloxycarbonylamino-$(C_1-C_4)$-alkyl, carboxy-$(C_1-C_{10})$-alkyl, $(C_1-C_4)$-alkoxycarbonyl-$(C_1-C_{10})$-alkyl;

$R^2$ denotes hydrogen; $(C_1-C_6)$-alkyl which can optionally be substituted by amino, $(C_1-C_6)$-acylamino or benzoylamino; $(C_2-C_6)$-alkenyl, $(C_3-C_9)$-cycloalkyl, $(C_5-C_9)$-cycloalkenyl, $(C_3-C_7)$-cycloalkyl$(C_1-C_4)$-alkyl, $(C_6-C_{12})$-aryl or partially hydrogenated aryl, each of which can be substituted by $(C_1-C_4)$-alkyl, $(C_1$ or $C_2)$-alkoxy or halogen; $(C_6-C_{12})$-aryl-$(C_1-C_4)$-alkyl or $(C_7-C_{13})$-aroyl-$(C_1-C_2)$-alkyl, both of which can be substituted in the aryl radical as defined above; a mono- or bicyclic heterocyclic radical having 5 to 7 or 8 to 10 ring atoms, respectively, of which 1 to 2 ring atoms represent sulfur or oxygen atoms and/or 1 to 4 ring atoms represent nitrogen atoms; or a side-chain of a naturally occurring, optionally protected α-amino acid; but especially hydrogen; $(C_1-C_3)$-alkyl; $(C_2$ or $C_3)$-alkenyl; the optionally protected side-chain of lysine; benzyl, 4-methoxybenzyl, 4-ethoxybenzyl, phenethyl, 4-aminobutyl or benzoylmethyl, and $R^3$ and $R^4$ form, together with the atoms carrying them, a bi- or tricyclic heterocyclic ring system from the series comprising octahydroindole, octahydrocyclopenta[b]pyrrole, spiro[(bicyclo[2.2.2]octan)-2,3'-pyrrolidine], 1,2,3,3a,4,6a-hexahydrocyclopenta[b]pyrrole or indoline.

If $R^2$ represents a side-chain of a protected naturally occurring α-amino acid, such as, for example, protected Ser, Thr, Asp, Asn, Glu, Gln, Arg, Lys, Hyl, Cys, Orn, Cit, Tyr, Trp or His, the preferred protective groups are the groups customary in peptide chemistry (cf. Houben-Weyl, Vol. XV/1 and XV/2). In the case where $R^1$ denotes the protected lysine side-chain, the known amino protective groups, but especially Z, Boc or $(C_1-C_6)$-alkanoyl, are preferred. Suitable and preferred as 0-protective groups for tyrosine are $(C_1-C_6)$-alkyl, especially methyl or ethyl.

The invention also relates to a process for the preparation of a compound of the formula I, which comprises reacting together the fragments thereof in a suitable solvent, where appropriate in the presence of a base and/or of an aid to coupling, where appropriate reducing unsaturated compounds produced as intermediates, such as Schiff's bases, eliminating protective groups temporarily introduced to protect reactive groups, subjecting the compounds obtained in this way to intramolecular cyclization, where appropriate esterifying compounds of the formula I with free carboxyl group(s), and where appropriate converting the resulting compounds into the physiologically tolerated salts thereof.

It is possible, for example, to react in the stated manner compounds of the formula II and III with the formation of compounds of the formula IV

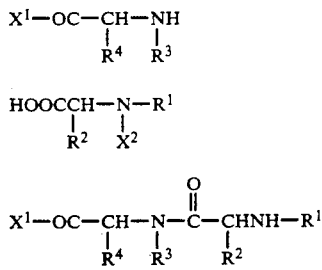 (II)

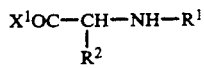 (III)

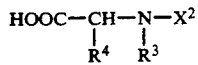 (IV)

in which $R^1$ to $R^4$ is defined in the manner indicated above; $X^1$ represents $(C_1-C_8)$-alkoxy, $(C_7-C_{13})$-arylalkoxy, $(C_1-C_4)$-alkylamino, $(C_7-C_{13})$-arylalkylamino, but preferably represents methoxy, ethoxy, benzyloxy, tert.-butoxy, as protective group which is temporarily introduced for the carboxyl groups which is not involved in the reaction, and which can be eliminated in a manner known per se after the reaction is complete; and $X^2$ represents the protective groups which are known in peptide synthesis for amino groups (cf. Houben-Weyl, Meth. d. organ. Chemie Volume XV 1 and 2; Greene, "Protective Groups in Organic Synthesis", New York 1981), such as, for example, tert.-butoxycarbonyl, fluorenylmethoxycarbonyl, benzyloxycarbonyl, which can be eliminated again in a manner known per se after the reaction has taken place.

The intramolecular cyclization of the compounds of the formula IV in the stated manner to give the compounds of the formula I according to the invention can take place either with the group $X^1$ or after separate elimination of $X^1$ to give the carboxyl group.

The reaction of these compounds can be carried out, for example, in analogy to known peptide-coupling methods in an organic solvent such as DMF, $CH_2Cl_2$, DMA and in the presence of aids to coupling, such as carbodiimides (for example dicyclohexylcarbodiimide), diphenylphosphoryl azide, alkanephosphonic anhydrides, dialkylphosphinic anhydrides or N,N'-disuccinimidyl carbonate in a solvent such as $CH_3CN$. Amino groups in compounds of the formula II can be activated with tetraethyl diphosphite. The compounds of the formula III can be converted into active esters (for example with 1-hydroxybenzotriazole), mixed anhydrides (for example with chloroformic esters), azides or carbodiimide derivatives and thus be activated (cf. Schroder, Lubke, The Peptides, Volume 1, New York 1965, pages 76–136). The reaction is preferably carried out at between $-20°$ C. and the boiling point of the reaction mixture.

However, the reaction to give compounds of the formula IV can also be carried out thermally in a suitable organic solvent in the temperature range between $0°$ C. and the boiling point of the solvent.

It is likewise possible for compounds of the formula V and VI to be linked together in the stated manner to give compounds of the formula VII and subsequently cyclized to give compounds of the formula I.

$X^1OC-CH-NH-R^1$ (V)
$\quad\quad\quad|$
$\quad\quad\quad R^2$ $HOOC-CH-N-X^2$ (VI)
$\quad\quad\quad|\quad\;|$
$\quad\quad\;R^4\;R^3$

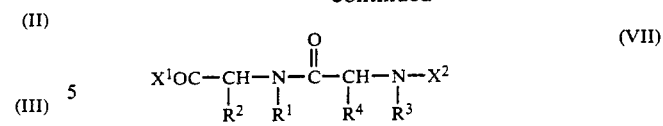 (VII)

It is likewise also possible to react compounds of the formula VIII with compounds of the formula IX, with the formation of compounds of the formula IV

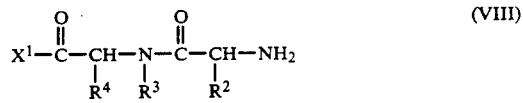 (VIII)

 (IX)

in which $R^1$, $R^2$, $R^3$, $R^4$ and $X^1$ are as defined above, and $Y^1$ represents a leaving group. Examples of suitable leaving groups are Cl, Br, I, alkylsulfonyloxy or arylsulfonyloxy.

An alkylation of this type is expediently carried out in water or an organic solvent such as dichloromethane or another aliphatic alcohol (such as ethanol), benzyl alcohol, acetonitrile, nitromethane or glycol ether, at a temperature between $-20°$ C. and the boiling point of the reaction mixture, in the presence of a base—such as an alkali metal hydroxide or an organic amine.

It is also possible, for example, for the new compounds of the general formula I to be prepared by use of alkylation methods familiar to those skilled in the art (see, for example, Houben-Weyl, Methoden der organischen Chemie (Methods of Organic Chemistry) Volume E 5), for example the reaction of a compound of the formula I in which at least one of the radicals $R^1$ and $R^3$ denotes hydrogen with an appropriate alkylating agent of the general formula IX, such as, for example, an alkyl halide, under basic catalysis in a polar protic or dipolar aprotic solvent.

The nootropic action of the compounds according to the invention was tested on mice, which had a body weight of 20–25 g, in the inhibitory (passive) avoidance test (step-through model). A modified form of the test method described by J. KOPP, Z. BODANECKY and M. E. JARVIK has been described by J. BURES, O. BURESOVA and J. HUSTON in "Techniques and Basic Experiments for the Study of Brain and Behavior", Elsevier Scientific Publishers, Amsterdam (1983).

According to the statements in this literature, a substance is designated as having nootropic activity when it is able to abolish the amnesia produced in the experimental animals by means of an electroconvulsive shock or the amnesia induced by scopolamine.

The experiments were carried out by modified test methods. The comparison compound used was the known nootropic agent 2-oxo-1-pyrrolidinylacetamide (piracetam). The distinct superiority of the compounds according to the invention over the comparison substance was evident from the fact that it is possible to abolish the scopolamine-induced amnesia in the inhibitory avoidance test with an oral MED (minimal effective dose) of 1.0–30 mg/kg. The comparison substance has an oral MED of about 500–1,000 mg/kg.

The compounds according to the invention have, in general, only low toxicity and are suitable, by reason of their pharmacological properties, for the treatment of cognitive dysfunctions of various etiologies as occur, for example, in Alzheimer's disease or senile dementia.

The invention additionally embraces pharmaceuticals containing the said compounds, processes for the preparation thereof, and the use of the compounds according to the invention in the preparation of pharmaceuticals which are used for the treatment and prophylaxis of the above-mentioned diseases.

The pharmaceuticals are prepared by processes which are known per se and are familiar to those skilled in the art. The pharmacologically active compounds (=active substance) according to the invention are used as pharmaceuticals either as such or, preferably, in combination with suitable pharmaceutical auxiliaries in the form of tablets, coated tablets, capsules, suppositories, emulsions, suspensions or solutions, with the content of active substance being up to about 95%, advantageously between 10 and 75%.

The particular auxiliaries suitable for the desired pharmaceutical formulation are familiar to those skilled in the art on the basis of their expert knowledge. Besides solvents, gel-formers, suppository bases, tablet auxiliaries and other active substance vehicles, it is possible to use, for example, antioxidants, dispersants, emulsifiers, antifoam agents, flavorings, preservatives, solubilizers or colorants.

The active substances can be administered, for example, orally, rectally or parenterally (for example intravenously or subcutaneously), with oral administration being preferred.

For a form for oral use, the active compounds are mixed with the additives suitable for this purpose, such as excipients, stabilizers or inert diluents and are converted by customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, lactose, glucose or starch, especially corn starch. This preparation can be carried out both as dry and as wet granules. Examples of suitable oily excipients or solvents are vegetable or animal oils, such as sunflower oil or fish liver oil.

For subcutaneous or intravenous administration, the active compounds, or the physiologically tolerated salts thereof, are converted into solution, suspension or emulsion, if desired with the substances customary for this purpose, such as solubilizers, emulsifiers or other auxiliaries. Examples of suitable solvents are water, physiological saline or alcohols, for example ethanol, propanol and glycerol, as well as sugar solutions such as glucose or mannitol solutions, or else a mixture of the various solvents mentioned.

Example 1

(3S,5S,8aS,9aS)-3-Methyl-2H-decahydrocyclopenta[4,5]-pyrrolo[1,2-a]pyrazine-1,4-dione a) To 41.2 g of benzyl (1S,3S,5S)-2-azabicyclo[3.3.0]-octanecarboxylate and 34.8 g of N-tert.-butoxycarbonyl-L-alanine in 680 ml of dimethylformamide were added, at −5° C., 116 ml of triethylamine and 170 ml of a 50% strength solution of n-propylphosphonic anhydride (n-PropPA) in $CH_2Cl_2$, and the mixture was stirred at room temperature overnight. The reaction solution was diluted with 1 l of ethyl acetate and washed twice with saturated $NaHCO_3$ solution, twice with 10% strength citric acid solution and once with saturated NaCl solution, dried with $MgSO_4$ and concentrated to an oily consistency in vacuo. The yield was 65.9 g of a colorless oil.

$[\alpha]_D^{20} = -52.2°$ (c=1 in methanol)

b) 14.6 g of the benzyl 2-(N-tert.-butoxycarbonyl-S-alanyl)-(1S,3S,5S)-2-azabicyclo[3.3.0]octanecarboxylate described under a) were stirred with 25 ml of trifluoroacetic acid at 0° C. for thirty minutes and then at room temperature for two hours. The solution was concentrated in vacuo, and renewed concentration was carried out three times after addition of 10 ml of toluene each time. The residue obtained in this way was refluxed in 100 ml of ethyl acetate for 9 hours. After the reaction solution was cooled, 4.06 g of colorless crystals of melting point 222° C. were obtained.

$[\alpha]_D^{20} = +3.12°$ (c=1 in methanol)

Example 2

(3S,5R,8aR,9aR)-3-Methyl-2H-decahydrocyclopenta[4,5]-pyrrolo-[1,2-a]pyrazine-1,4-dione a) Benzyl 2-(N-tert.-butoxycarbonyl-S-alanyl)-(1R,3R,5R)-2-azabicyclo[3.3.0]octanecarboxylate 4.91 g of benzyl (1R,3R,5R)-2-azabicyclo[3.3.0]octanecarboxylate and 4.12 g of N-tert.-butoxycarbonyl-L-alanine were dissolved in 80 ml of absolute dimethylformamide and, at 0° C., 12.7 ml of N-ethylmorpholine and 20.2 ml of n-propylphosphonic anhydride (50% in $CH_2Cl_2$) were added. The reaction mixture was stirred at room temperature for 5 hours. After addition of 120 ml of ethyl acetate, the mixture was washed twice with saturated $NaHCO_3$ solution, twice with 10% strength citric acid solution and once with saturated brine. Remaining after drying and concentration of the organic phases were 8.04 g of a viscous oil.

$[\alpha]_D^{20} = 97.2°$ (c=1 in methanol)

b) 7 g of the oil obtained under a) were hydrogenated with Pd on charcoal in 290 ml of ethanol at room temperature. Remaining after the catalyst had been filtered off and the solution had been concentrated were 5.5 g of a colorless solid of melting point 140° C.

c) 1 g of the carboxylic acid obtained under b) were treated with 5 ml of trifluoroacetic acid at 0° C. for 45 minutes. The solid residue obtained after concentration was refluxed in isopropanol for 9 hours. The solvent was stripped off in vacuo, and the residue was recrystallized from ethyl acetate. 435 mg of colorless crystals were obtained. Melting point 214° C.

EXAMPLE 3

(3S,5S,8aS,9aS)-3-Cyclohexylmethyl-2H-decahydrocyclopenta[4,5]pyrrolo-[1,2-a]pyrazine-1,4-dione a) 5.7 g of N-tert.-butoxycarbonyl-L-cyclohexylalanine and 5.5 g of benzyl (1S,3S,5S)-2-azabicyclo[3.3.0]octanecarboxylate were dissolved in 55 ml of $CH_2Cl_2$/DMF 10:1 and, at 0° C., 15 ml of N-ethylmorpholine and 24 ml of n-propylphosphonic anhydride (50% strength in $CH_2Cl_2$) were added. The reaction solution was stirred at room temperature overnight, diluted with 150 ml of $CH_2Cl_2$ and extracted with saturated $NaHCO_3$, 10% strength citric acid and saturated brine. After the organic phase had been dried and concentrated, a brown oil was obtained and was purified by column chromatography (silica gel, cyclohexane/ethyl acetate). The yield was 7.9 g of colorless oil.

$[\alpha]_D^{20} = -29.9°$ (c=1 in methanol)

b) 1.5 g of the oil obtained under a) was dissolved in 7 ml of dimethoxyethane saturated with hydrogen chloride, and the solution was stirred at room temperature for 0.5 hours. The solution was evaporated to dryness. The residue was taken up in 20 ml of iso-propanol and refluxed for 6 hours. After the solution had been cooled, 450 mg of colorless crystals were obtained by filtration with suction.

Melting point 239° C.

Example 4

(3S,5S,8aS,9aR)-3-Methyl-2N-(3-phenylpropyl)-2H-decahydrocyclopenta[4,5]pyrrolo[1,2-a]pyrazine-1,4-dione 1 g of the piperazine-2,5-dione described in Example 1 was dissolved in 20 ml of dimethylformamide at 0° C., and 0.56 g of potassium tert.-butylate was added. A reaction time of 45 minutes resulted in a clear yellow solution, to which 0.73 ml of 3-phenylpropyl bromide was added dropwise. After 2 hours at 0° C. the solution was warmed to room temperature and then poured into water, the mixture was extracted three times with ethyl acetate, and the organic phase was dried and concentrated. Purification by chromatography (silica gel, cyclohexane/ethyl acetate) resulted in 1.04 g of colorless crystals.

Melting point 92° C.
$[\alpha]_D^{20} = +127.5°$ (c=1 in methanol)

Example 5

(3S,5S,8aS,9aR)-3-Methyl-2N-octyl-2H-decahydrocyclopenta-[4,5]pyrrolo[1,2-a]pyrazine-1,4-dione 2 g of the piperazine-2,5-dione described in Example 1 were dissolved in 50 ml of DMF and, while cooling in ice, 1.12 g of potassium tert.-butylate were added. After 40 minutes, 1.66 ml of n-octyl bromide were added dropwise, and the reaction mixture was stirred overnight. The solution was diluted with water and extracted several times with ethyl acetate. The organic phase was dried and concentrated, leaving a residue of 3.3 g of oily crude product. Purification by chromatography on silica gel (cyclohexane/ethyl acetate) yielded 1.1 g of desired product of melting point 44°-47° C.

$[\alpha]_D^{20} = +156.1°$ (c=1 in methanol)

Example 6

(3S,5S,8aS,9aS)-3-Methyl-2N-(1-S-ethoxycarbonylheptyl)-2H-decahydrocyclopenta[4,5]pyrrolo[1,2-a]pyrazine-1,4-dione a) N-(1-R,S-Ethoxycarbonylheptyl)-L-alanine benzyl ester 7.56 g of L-alanine benzyl ester x p-toluenesulfonic acid are dissolved in 200 ml of dichloromethane and, at 0° C., 8.6 ml of triethylamine and subsequently 6.2 g of ethyl 2-trifluoromethanesulfonyloxyoctanoate are added, and the mixture is stirred for 24 hours. The reaction solution was concentrated, the residue was taken up in ethyl acetate, and the solution was washed with NH$_4$Cl solution and NaCl solution, dried with MgSO$_4$ and concentrated. The resulting 6.2 g of crude product was separated into the two diastereomeric products by column chromatography (silica gel, cyclohexane/ethyl acetate). The less polar diastereomer was obtained in a yield of 2.2 g. The more polar diastereomer was obtained in a yield of 1.6 g.

$[\alpha]_D^{20} = -31.2°$ (c=1 in methanol)

b) N-(1-S-Ethoxycarbonylheptyl)-L-alanine 3.2 g of benzyl ester (polar diastereomer) were hydrogenated on 900 mg of palladium/charcoal in 130 ml of ethanol. After the reaction was complete, the catalyst was removed by filtration, and the solvent was removed by distillation in vacuo. The yield was 2.2 g.

$[\alpha]_D^{20} = +9.2°$ (c=1 in methanol)

c) Benzyl 2-[N-(1-S-ethoxycarbonylheptyl)-S-alanyl]-(1S,3S,5S)-2-azabicyclo[3.3.0]octane-3-carboxylate 2.3 g of the carboxylic acid obtained in b), and 2.3 g of benzyl (1S,3S,5S)-2-azabicyclo[3.3.0]octane-3-carboxylate were dissolved in 110 ml of absolute dimethylformamide and, at −8° C., 6.0 ml of triethylamine and 8.2 ml of n-propylphosphonic anhydride were added. After stirring at room temperature for 48 hours, the solution was diluted with ethyl acetate, washed with saturated NaHCO$_3$ solution, 10% citric acid and saturated NaCl solution, dried over MgSO$_4$ and concentrated. The 3.9 g of crude product was purified by column chromatography on silica gel (cyclohexane/ethyl acetate) and yielded 1.2 g of pure substance.

$[\alpha]_D^{20} = -46.6°$ (c=1 in methanol)

d) 2-[N-(1-S-Ethoxycarbonylheptyl)-S-alanyl]-(1S,3S,5S)-2-azabicyclo[3.3.0]octane-3-carboxylic acid 1.2 g of the above ester (see c)) were hydrogenated on 250 mg of palladium/charcoal in 50 ml of ethanol. After the reaction was complete, the catalyst was removed by filtration, and the solution was concentrated. The yield was 910 mg.

$[\alpha]_D^{20} = +5.3°$ (c=1 in methanol)

e) 400 mg of the carboxylic acid obtained in d) were dissolved together with 156 mg of 1-hydroxybenzotriazole and 208 mg of dicyclohexylcarbodiimide in 10 ml of DMF and stirred overnight. The solution was filtered to remove precipitated dicyclohexylurea and was mixed with ethyl acetate, washed with saturated NaHCO$_3$ solution, 10% citric acid and saturated NaCl solution, dried over MgSO$_4$ and concentrated. The crude product was stirred with petroleum ether, and the resulting crystals were filtered off with suction. The yield was 170 mg.

$[\alpha]_D^{20} = -41.1°$ (c=1 in methanol)

Example 7

(3S,5S,8aS,9aS)-3-Methyl-2N-(1-R-ethoxycarbonylheptyl)-2H-decahydrocyclopenta[4,5]pyrrolo[1,2-a]pyrazine-1,4-dione The less polar diastereomer obtained in Example 6a) was reacted in analogy to the descriptions in 6b)-d). 550 mg of 2-[N-(1-R-ethoxycarbonylheptyl)-S-alanyl]-(1S,3S,5S)-2-azabicyclo[3.3.0]octane-3-carboxylic acid ($[\alpha]_D^{20} = +4.4°$, (c=1 in methanol) were reacted with 215 mg of 1-hydroxybenzotriazole and 290 mg of dicyclohexylcarbodiimide in 14 ml of absolute dimethylformamide. The reaction was complete after stirring at room temperature for 48 hours. The working up was carried out as described in Example 6e). The yield was 330 mg of colorless oil.

$[\alpha]_D^{20} = -3.7°$ (c =1 in methanol)

Example 8

(3S,6S,7aS)-3-Methyl-6-exo-spiro(bicyclo[2.2.2]octan-2-yl)-2N-(1-S-ethoxycarbonyl-3-phenylpropyl)octahydropyrrolo[1,2-a]pyrazine-1,4-dione 0.4 g of N-(1-S-ethoxycarbonyl-3-phenylpropyl)-S-alanyl-exo-spiro(bicyclo[2.2.2]octane-2,3-pyrrolidin)-5-yl-carboxylic acid in 5 ml of absolute DMF was stirred together with 130 mg of 1-hydroxybenzotriazole and 175 mg of dicyclohexylcarbodiimide at room temperature overnight. The precipitated dicyclohexylurea was removed by filtration and the filtrate was diluted with ethyl acetate, washed with 5% NaHCO$_3$ solution, 10% citric acid and saturated NaCl solution and subsequently dried over MgSO$_4$. The crude product remaining after distillation was chromatographed on silica gel (cyclohexane/ethyl acetate). The yield was 0.2 g of desired product. Mass spectrum: m/e=452 M+

We claim:

1. A compound of formula I

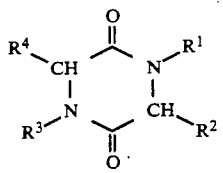

in which

R$^1$ denotes hydrogen or (C$_1$–C$_8$)-alkyl, wherein said (C$_1$–C$_b$)-alkyl can be substituted by (C$_1$–C$_4$)-alkylcarbonyl and/or phenyl;

R$^2$ denotes (C$_1$–C$_8$)-alkyl or (C$_3$–C$_8$)-cycloalkyl-(C$_1$–C$_4$)-alkyl and R$^3$ and R$^4$ form together with the atoms carrying them a ring system selected from the groups B, C, D, G and H

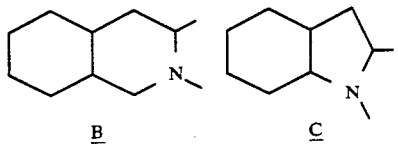

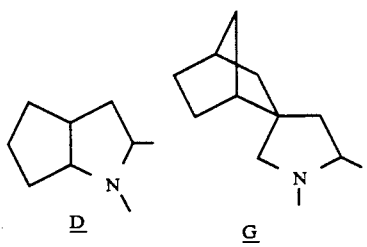

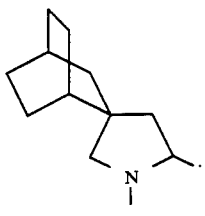

2. A compound which is (3S,5S,8aS,9aS)-3-methyl-2H-decahydrocyclopenta[4,5]-pyrrolo[1,2-a]pyrazine-1,4-dione.

3. The compound of the formula I as claimed in claim 1 wherein is (3S,5R,8aR,9aR)-3-methyl-2H-decahydrocyclopenta[4,5]-pyrrolo-[1,2-a]pyrazine-1,4-dione.

4. The compound of the formula I as claimed in claim 1 which is (3S,5S,8aS,9aS)-3-cyclohexylmethyl-2H-decahydrocyclopenta[4,5]pyrrolo-[1,2-a]pyrazine-1,4-dione.

5. The compound of the formula I as claimed in claim 1 which is (3S,5S,8aS,9aR)-3-methyl-2-N(3-phenylpropyl)-2H-decahydrocyclopenta[4,5]pyrrolo[1,2-a]pyrazine-1,4-dione.

6. The compound of the formula I as claimed in claim 1 which is (3S,5S,8aS,9aR)-3-methyl-2N-octyl-2H-decahydrocyclopenta[4,5]pyrrolo[1,2-a]pyrazine-1,4-dione.

7. The compound of the formula I as claimed in claim 1 which is (3S,5S,8aS,9aS)-3-methyl-2N-(1-S-ethoxycarbonylheptyl)-2H-decahydrocyclopenta[4,5]pyrrolo[1,2-a]pyrazine-1,4-dione.

8. The compound of the formula I as claimed in claim 1 which is (3S,5S,8aS,9aS)-3-methyl-2N-(1-R-ethoxycarbonylheptyl)-2H-decahydrocyclopenta[4,5]pyrrolo[1,2-a]pyrazine-1,4-dione.

9. The compound of the formula I as claimed in claim 1 which is (3S,6S,7aS)-3-methyl-6-exo-spiro(bicyclo[2.2.2]octan-2-yl)-2N-(1-S-ethoxycarbonyl-3-phenylpropyl)octahydro-pyrrolo[1,2-a]pyrazine-1,4-dione.

10. A pharmaceutical composition comprising a nootropically effective amount of a compound of the formula I as claimed in claim 1 or a pharmaceutical acceptable salt thereof.

11. A method of treating a cognitive dysfunction comprising administering a nootropically effective amount of a compound of the formula I as claimed in claim 1 or a physiologically tolerated salt thereof.

* * * * *

UNITED STATES PATENT AND TRADEMARK OFFICE
CERTIFICATE OF CORRECTION

PATENT NO. : 5,091,427
DATED : February 25, 1992
INVENTOR(S) : Wolf-Ulrich Nickel et al.

It is certified that error appears in the above-identified patent and that said Letters Patent is hereby corrected as shown below:

Claim 1, Column 13, Line 24, "$(C_1-C_b)$-alkyl" should read --$(C_1-C_8)$-alkyl--

Claim 1, Column 13, Line 28, before "and" insert --;--

Claim 3, Column 14, Line 17, "wherein" should read --which--

Claim 5, Column 14, Line 24, "which is (3S,5S,8aS,9aR)-3-methyl-2-N(3-phenyl-" should read --which is (3S,5S,8aS,9aR)-3-methyl-2-N-(3-phenyl---

Signed and Sealed this

Fourteenth Day of December, 1993

Attest:

BRUCE LEHMAN

Attesting Officer    Commissioner of Patents and Trademarks